United States Patent
Lu et al.

(10) Patent No.: US 10,696,617 B2
(45) Date of Patent: Jun. 30, 2020

(54) METHOD FOR ALCOHOLYSIS OF AMIDE

(71) Applicant: ASYMCHEM LABORATORIES (TIANJIN) CO., LTD, Tianjin (CN)

(72) Inventors: Jiangping Lu, Tianjin (CN); Qinglan Pei, Tianjin (CN); Jinquan Yu, Tianjin (CN); Enxuan Zhang, Tianjin (CN)

(73) Assignee: ASYMCHEM LABORATORIES (TIANJIN) CO., LTD, Tianjin (CN)

( * ) Notice: Subject to any disclaimer, the term of this patent is extended or adjusted under 35 U.S.C. 154(b) by 0 days.

(21) Appl. No.: 16/609,237

(22) PCT Filed: May 8, 2017

(86) PCT No.: PCT/CN2017/083498
§ 371 (c)(1),
(2) Date: Oct. 29, 2019

(87) PCT Pub. No.: WO2018/205108
PCT Pub. Date: Nov. 15, 2018

(65) Prior Publication Data
US 2020/0055807 A1    Feb. 20, 2020

(51) Int. Cl.
*C07C 67/20*    (2006.01)

(52) U.S. Cl.
CPC .................................. *C07C 67/20* (2013.01)

(58) Field of Classification Search
CPC ...................................................... C07C 67/20
See application file for complete search history.

(56) References Cited

U.S. PATENT DOCUMENTS

| | | | |
|---|---|---|---|
| 4,990,651 A | 2/1991 | Ikarashi | |
| 2010/0160669 A1 | 6/2010 | Liu | |

FOREIGN PATENT DOCUMENTS

| | | |
|---|---|---|
| CN | 101448774 A | 6/2009 |
| CN | 101468947 A | 7/2009 |
| CN | 102239134 A | 11/2011 |
| CN | 104109099 A | 10/2014 |
| EP | 0945423 A2 | 9/1999 |

OTHER PUBLICATIONS

Daniels et al, Organic Letters, Sequential Regioselective C—H Functionalization of Thiophenes, 2016, pp. 3310-3313. (Year: 2016).*
International Search Report for corresponding application PCT/CN2017/083498 filed May 8, 2017; dated Jul. 6, 2017.

* cited by examiner

*Primary Examiner* — Paul A Zucker
(74) *Attorney, Agent, or Firm* — Cantor Colburn LLP

(57) ABSTRACT

Provided is a method for the alcoholysis of an amide. The method comprises subjecting an amide-containing compound to alcoholysis under alkaline conditions using an epoxy compound as an accelerant of alcoholysis, the method comprising: mixing the amide-containing compound, the epoxy compound, a pH adjuster and a solvent to form an alkaline reaction system, the pH of the alkaline reaction system being 7.5-9.5; reacting the alkaline reaction system at 50° C. ~150° C. to subject the amide-containing compound to alcoholysis.

12 Claims, No Drawings

METHOD FOR ALCOHOLYSIS OF AMIDE

TECHNICAL FIELD

The application relates to the field of organic material synthesis, in particular to a method of amide alcoholysis.

BACKGROUND

As a common functional group, an amide bond is widely present in natural products such as proteins and synthetic compounds. It is generally believed that the resonance stability of the amide bond makes the amide a weak electrophile (The structure of proteins: two hydrogenbonded helical configurations of the polypeptide chain. Proc. Natl. Acad. Sci. 1951, 37, 205), accordingly, it is difficult to selectively open the C—N bond of the amide by chemical synthesis (Conversion of amides to esters by the nickel-catalysed activation of amide C—N bonds. Nature 2015, 524, 79).

—CONHAr$_F$ (Ar$_F$=p-CF$_3$C$_6$F$_4$) is an excellent amide-guiding group and has a wide range of applications in various types of β-C—H activation reactions, but its disadvantage is that for certain substrates, the guiding group is difficult to remove (Ligand-Enabled β-C—H Arylation of α-Amino Acids Using a Simple and Practical Auxiliary. J. Am. Chem. Soc. 2015, 137, 3338). This greatly limits the further conversion utilization of these C—H activation products, so it is necessary to develop a universal method for removing the guiding group.

Existing methods for removing the guiding group: 1. heating a strong alkali aqueous solution to hydrolyze the amide to a carboxylic acid; 2. heating a strong acid to hydrolyze the amide to a carboxylic acid; 3. adding NaNO$_2$ in a mixed solvent Ac$_2$O/AcOH to obtain a carboxylic acid; 4. obtaining by heating BF$_3$.Et$_2$O in methanol; 5. forming an ester through Hydrolysis by stepwise reaction of LiHMDS/MeOCOCl/MeONa.

For the above method of using BF$_3$.Et$_2$O, the reaction is carried out at 100° C. to achieve alcoholysis of the guiding group, and the method has the disadvantages of expensive reagents, complicated operation and harsh reaction conditions. The remaining methods described above require strong acid or strong base conditions and many functional groups are not stable under these conditions. Moreover, the above methods are all obviously affected by the substrate steric hindrance, and the substrate has a small application range.

SUMMARY

The main object of the present application is to provide a method for amide alcoholysis, so as to solve the problems of complicated operation and harsh reaction conditions of the amide alcoholysis method in the prior art.

In order to achieve the above object, according to one aspect of the present application, a method for amide alcoholysis is provided, the method comprises subjecting an amide-containing compound to alcoholysis under alkaline conditions using an epoxy compound as an accelerant of alcoholysis.

Further, calculated in the molar ratio of the epoxy compound to an amide group, the ratio of the epoxy compound used to the amide-containing compound used is 1-5:1.

Further, the amide-containing compound has a formula I, the formula I is

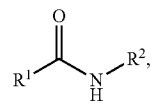

wherein the R$^1$, and the R$^2$ are each independently selected from any one of an alkyl group, an aryl group, a substituted alkyl group and a substituted aryl group; preferably, the alkyl group is selected from any one of C$_1$~C$_{18}$ alkyl groups, and preferably the substituted alkyl group has a main chain carbon number of any one of C$_1$~C$_{18}$, and preferably the substituted alkyl group is a monosubstituted alkyl group or a polysubstituted alkyl group, preferably the substituent in the substituted alkyl group is selected from any one or a combination of more of a group of an aryl group, an aromatic heterocyclic substituent, a cycloalkane group, a heterocycloalkane group, an alkenyl group and an alkynyl group.

Further, the epoxy compound has a formula II, the formula II is

wherein the R$^3$ and the R$^4$ are each independently selected from any one of H, an alkyl group and an aryl group; preferably, the alkyl group is selected from any one of C$_1$~C$_{18}$ alkyl groups.

Further, the method comprises mixing the amide-containing compound, the epoxy compound, a pH adjuster and a solvent to form an alkaline reaction system, preferably the pH of the alkaline reaction system is 7.5-9.5; reacting the alkaline reaction system at 50° C.~150° C. to subject the amide-containing compound to alcoholysis.

Further, the pH adjuster is a weak acid or a weak base, and preferably the pH adjuster is selected from any one or more of a group of CF$_3$CO$_2$K, CF$_3$CO$_2$Na, CsOAc, KOAc, NaOAc, LiOAc, CsHCO$_3$, KHCO$_3$, NaHCO$_3$, LiHCO$_3$, CsF, KF, NaF, LiF, Cs$_2$CO$_3$, K$_2$CO$_3$, Na$_2$CO$_3$, Li$_2$CO$_3$, K$_2$HPO$_4$, Na$_2$HPO$_4$, Li$_2$HPO$_4$, K$_3$PO$_4$, Na$_3$PO$_4$, sodium benzoate, tetramethylethylenediamine, N—N diisopropylethylamine and triethylamine.

Further, the solvent is selected from any one or more of a group of methanol, ethanol, n-propanol, isopropanol, n-butanol, isobutanol, n-pentanol, isoamyl alcohol, ethylene glycol, glycerol, 1,2-dimethoxyethane, ethylene glycol diethyl ether, 2-methoxyethyl ether, 2-ethoxyethyl ether, and pyrrole.

Further, the amide-containing compound is

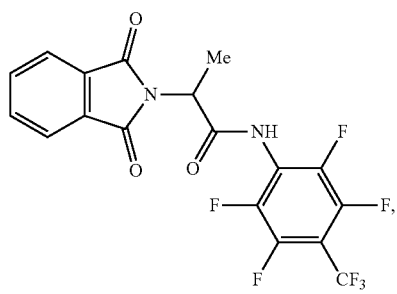 [SMILES: CC(C(=O)Nc1c(F)c(F)c(C(F)(F)F)c(F)c1F)N1C(=O)c2ccccc2C1=O]

the epoxy compound is methyl glycidyl ether, the pH adjuster is KOAc, and the solvent is ethanol.

Further, the alkaline reaction system is reacted at 80° C.~100° C. to subject the amide-containing compound to alcoholysis.

Further, after completion of alcoholysis, the method further comprises: removing the solvent of the alcoholysis product under reduced pressure to obtain a residue; mixing the residue with water to form a mixture; adjusting the pH of the mixture to 3.5~4.5 and extracting with n-hexane to obtain an organic phase; and drying and filtering the organic phase.

Further, after completion of alcoholysis, the method further comprises: removing the solvent of the alcoholysis product under reduced pressure to obtain a residue; purifying the residue by silica gel column chromatography.

Using the technical solution of the present application, the method described above is easy to operate; furthermore, for post-treatment, a pure product can be obtained only by means of a simple conventional separation step. Furthermore, due to the fact that the epoxy compound has a low cost, the production operation costs and the risk and cost of the treatment of three wastes can be greatly reduced. In addition, during use, the above-mentioned method has mild reaction conditions, is compatible with a variety of different substituents and functional groups, can achieve a good yield for amides of various structural types, and has a wide range of applicable substrates. That is, the present application provides an environmentally-friendly, economical and practical efficient method for alcoholysis of amide. The above-mentioned alcoholysis reaction of the present application is not affected by impurities in a C—H activation reaction system in the last step, thus saving an intermediate purification step, and the two steps of the reactions, i.e., C—H activation and amide alcoholysis, can be linked.

DETAILED DESCRIPTION OF THE EMBODIMENTS

The present application will be described in detail below in conjunction with embodiments. It should be noted that the embodiments in this application and the characteristics of the embodiments can be combined with each other if no conflict is caused.

As analyzed in the background art of the present application, although there are various amide alcoholisis methods in the prior art, the above methods have different defects. For example, in the method of using $BF_3 \cdot Et_2O$, when the reaction is carried out at 100° C. to achieve amide alcoholysis, the method has the disadvantages of expensive reagents, complicated operations, and harsh reaction conditions. To solve the problem, the present application provides a method for amide alcoholysis, the method comprises subjecting an amide-containing compound to alcoholysis under alkaline conditions using an epoxy compound as an accelerator of alcoholysis.

When studying removal of the guiding group from the amide compound, the inventor of the present application has unexpectedly discovered that the use of an alcohol solution of an epoxy compound under alkaline conditions can promote the conversion of an amide to an ester, and an amide N—H with a certain acidity nucleophilically attacks an open loop of the activated alkylene oxide under alkaline conditions to form an N-addition transition state product. The transition state is unstable. After the oxygen anion generated in situ nucleophilically attacks the carbonyl group of the amide bond upon opening of the loop of the alkylene oxide, the C—N bond of the amide group is broken, and the amide alcoholysis reaction is completed.

The method described above is easy to operate; furthermore, for post-treatment, a pure product can be obtained only by means of a simple conventional separation step. Furthermore, due to the fact that the epoxy compound has a low cost, the production operation costs and the risk and cost of the treatment of three wastes can be greatly reduced. In addition, during use, the above-mentioned method has mild reaction conditions, is compatible with a variety of different substituents and functional groups, can achieve a good yield for amides of various structural types, and has a wide range of applicable substrates. That is, the present application provides an environmentally-friendly, economical and practical efficient method for alcoholysis of amide. The above-mentioned alcoholysis reaction of the present application is not affected by impurities in a C—H activation reaction system in the last step, thus saving an intermediate purification step, and the two steps of the reactions, i.e., C—H activation and amide alcoholysis, can be linked.

In order to maximize the conversion rate of the amide and ensure the utilization of the epoxy compound, it is preferred that calculated in the molar ratio of the epoxy compound to an amide group, the ratio of the epoxy compound used to the amide-containing compound used is 1~5:1. Of course, when the ratio of the epoxy compound used to the amide-containing compound used is more than 5:1, alcoholysis can also be achieved, but many epoxy compounds are not involved in the reaction, resulting in waste of raw materials.

The substrate in the method of the present application has a wide universality and is not significantly affected by steric hindrance, and amide substrates of almost all structures can be smoothly reacted to obtain a good yield. Preferably, the amide-containing compound has a formula I, the formula I is

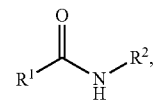

wherein the $R^1$, and the $R^2$ are each independently selected from any one of an alkyl group, an aryl group, a substituted alkyl group and a substituted aryl group; preferably, the alkyl group is selected from any one of $C_1$~$C_{18}$ alkyl groups, and preferably the substituted alkyl group has a main chain carbon number of any one of $C_1$~$C_{18}$, and preferably the substituted alkyl group is a monosubstituted alkyl group or a polysubstituted alkyl group, preferably the substituent in the substituted alkyl group is selected from any one or a combination of more of a group of an aryl group, an aromatic heterocyclic substituent, a cycloalkane, a heterocycloalkane, an alkenyl group and an alkynyl group. The substituent in the above substituted aryl group may be a halogen, an alkyl group, a substituted alkyl group or the like. For example, the $R^2$ is

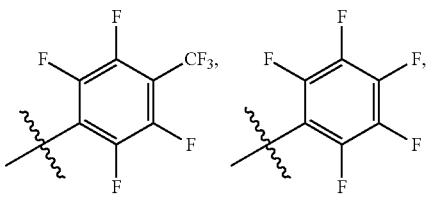

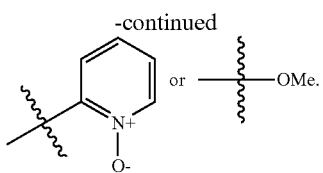

The amide-containing compound having the structure of the formula requires a mild reaction temperature and a short reaction time, and is suitable for large-scale industrial applications.

To further reduce the implementation cost of the above method, preferably the epoxy compound has a formula II, the formula II is

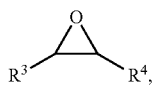

wherein the $R^3$ and the $R^4$ are each independently selected from any one of H, an alkyl group and an aryl group; preferably, the alkyl group is selected from any one of $C_1$~$C_{18}$ alkyl groups.

When the alcoholysis is carried out by using an epoxy compound as an accelerant, the alcoholysis process in the prior art can be referred to for the implementation process. Preferably, the method comprises mixing the amide-containing compound, the epoxy compound, a pH adjuster and a solvent to form an alkaline reaction system; reacting the alkaline reaction system at 50° C.~150° C. to subject the amide-containing compound to alcoholysis. Preferably, the pH of the alkaline reaction system is 7.5~9.5.

After the amide-containing compound and the epoxy compound are dispersed in a solvent, the alkaline reaction system is adjusted by a pH adjuster to make subsequent alcoholysis carried out smoothly and efficiently. In particular, when the pH of the alkaline reaction system is 7.5~9.5, the reaction rate is more ideal; then the reaction can be carried out at a low temperature of 50° C.~150° C. It can be seen from the above process that the method of the present application does not require special expensive reagents, requires only mild reaction conditions, and is applicable to a wide range of substrates.

The pH adjuster required for the above pH does not require strong acid or strong alkali, preferably, it is a weak acid or a weak base, and more preferably the pH adjuster is selected from any one of more of $CF_3CO_2K$, $CF_3CO_2Na$, CsOAc, KOAc, NaOAc, LiOAc, $CsHCO_3$, $KHCO_3$, $NaHCO_3$, $LiHCO_3$, CsF, KF, NaF, LiF, $Cs_2CO_3$, $K_2CO_3$, $Na_2CO_3$, $Li_2CO_3$, $K_2HPO_4$, $Na_2HPO_4$, $Li_2HPO_4$, $K_3PO_4$, $Na_3PO_4$, sodium benzoate, tetramethylethylenediamine, N—N diisopropylethylamine and triethylamine. Each of the above materials is inexpensive and the pH system formed is mild.

For the solvent of the present application, reference can be made to the solvent types commonly used in the prior art for amide alcoholysis. Preferably, the solvent is selected from any one or more of a group of methanol, ethanol, n-propanol, isopropanol, n-butanol, isobutanol, n-pentanol, isoamyl alcohol, ethylene glycol, glycerol, 1,2-dimethoxyethane, ethylene glycol diethyl ether, 2-methoxyethyl ether, 2-ethoxyethyl ether, and pyrrole.

The following is a description of the above reaction principle using KOAc as the pH adjuster and ethanol as the solvent. An amide N—H with a certain acidity nucleophilically attacks an open loop of the alkylene oxide activated by potassium ion under the action of KOAc to form an N-addition transition state product. The transition state is unstable. After the oxygen anion generated in situ nucleophilically attacks the carbonyl group of the amide bond upon opening of the loop of the alkylene oxide, the C—N bond of the amide group is broken to form an esterification intermediate product, and then the esterification intermediate and the alcohol solvent undergo a transesterification reaction to generate a final amide alcoholysis product. See the following chemical reaction process for details.

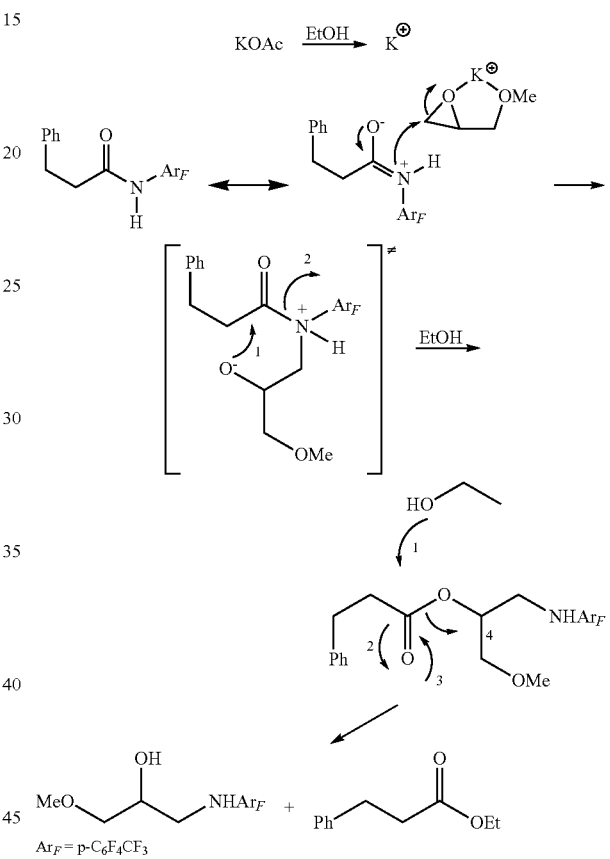

In a preferred embodiment of the present application, the amide-containing compound is

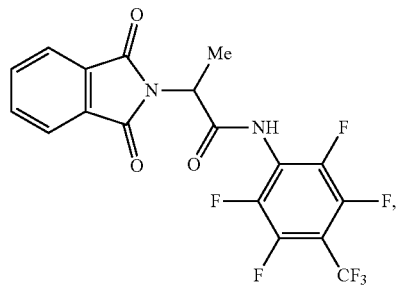 [SMILES: CC(C(=O)Nc1c(F)c(F)c(C(F)(F)F)c(F)c1F)N1C(=O)c2ccccc2C1=O]

the epoxy compound is methyl glycidyl ether, the pH adjuster is KOAc, and the solvent is ethanol.

When the method of the present application is applied to the alcoholysis of the above amide-containing compound, the final target product has a high yield.

In order to further accelerate the reaction rate and increase the yield, preferably the alkaline reaction system is reacted at 80° C.~100° C. to subject the amide-containing compound to alcoholysis.

In order to reduce the reaction cost, it is preferred to heat the reaction system with an oil bath.

After completion of the alcoholysis, preferably the method further comprises: removing the solvent of the alcoholysis product under reduced pressure to obtain a residue; mixing the residue with water to form a mixture; adjusting the pH of the mixture to 3.5~4.5 and extracting with n-hexane to obtain an organic phase; and drying and filtering the organic phase. Each of the materials used in the above process is a conventional material and therefore does not increase the cost for implementing the method of the present application. Moreover, the above process is a conventional operation in the purification process and therefore does not increase the complexity of the method of the present application. Further, controlling the pH value of the mixture at 3.5 to 4.5 at the time of extraction is beneficial to improving the extraction separation efficiency. For example, the pH value is adjusted to be acidic, such that the secondary amine structure on the leaving group is salted, the water solubility of the leaving group is enhanced, and by-products of the leaving group are easy to remove by washing. Strong acidity may deteriorate other functional groups on the product, and result in waste of the reagent. or, after completion of the alcoholysis, preferably the method further comprises: removing the solvent of the alcoholysis product under reduced pressure to obtain a residue; purifying the residue by silica gel column chromatography. This process is suitable for product separation in small batch trials of a laboratory.

The beneficial effects of the present application will be further described below in conjunction with the embodiments and comparative embodiments.

The amide-containing compounds used in the following embodiments are as follows:

a1
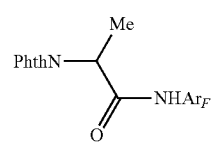

a2
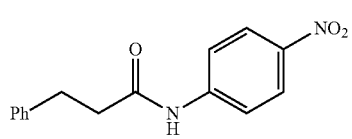

a3
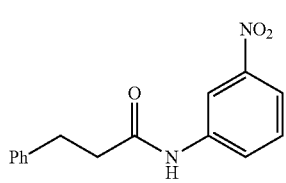

a4
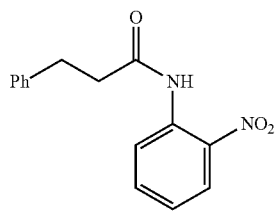

a5
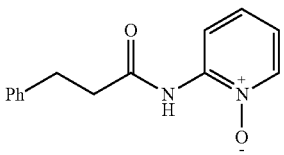

a6
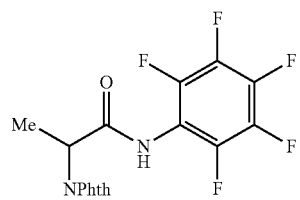

a7
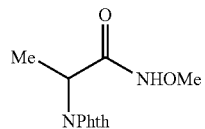

a8
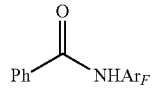

a9
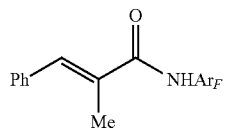

a10
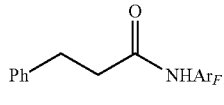

a11
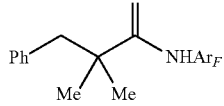

a12
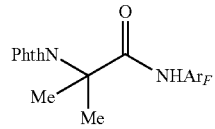

a13
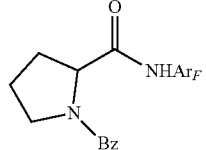

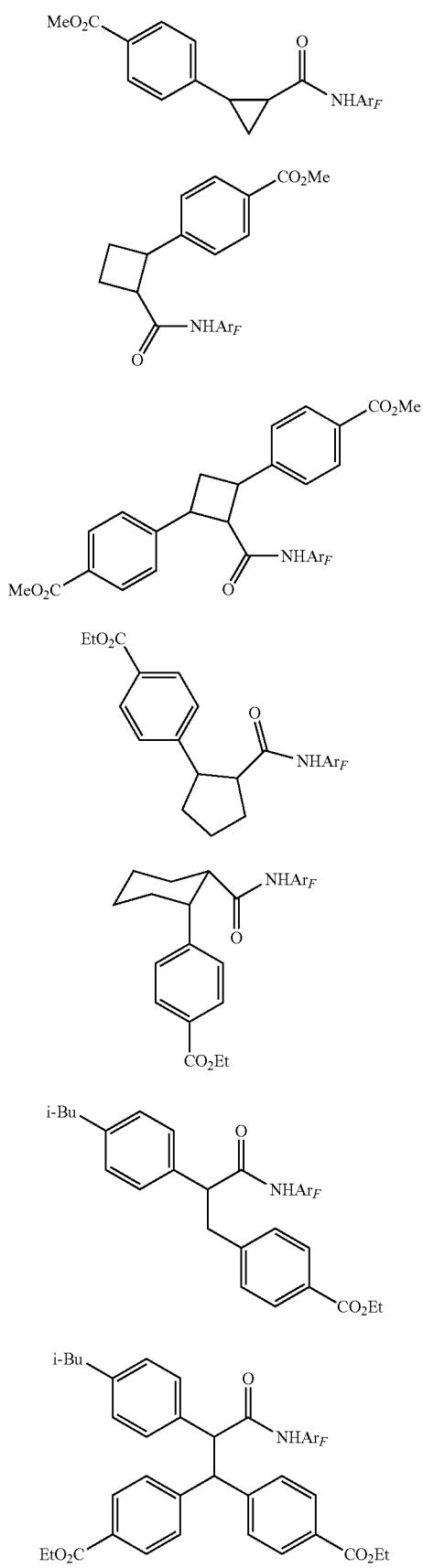
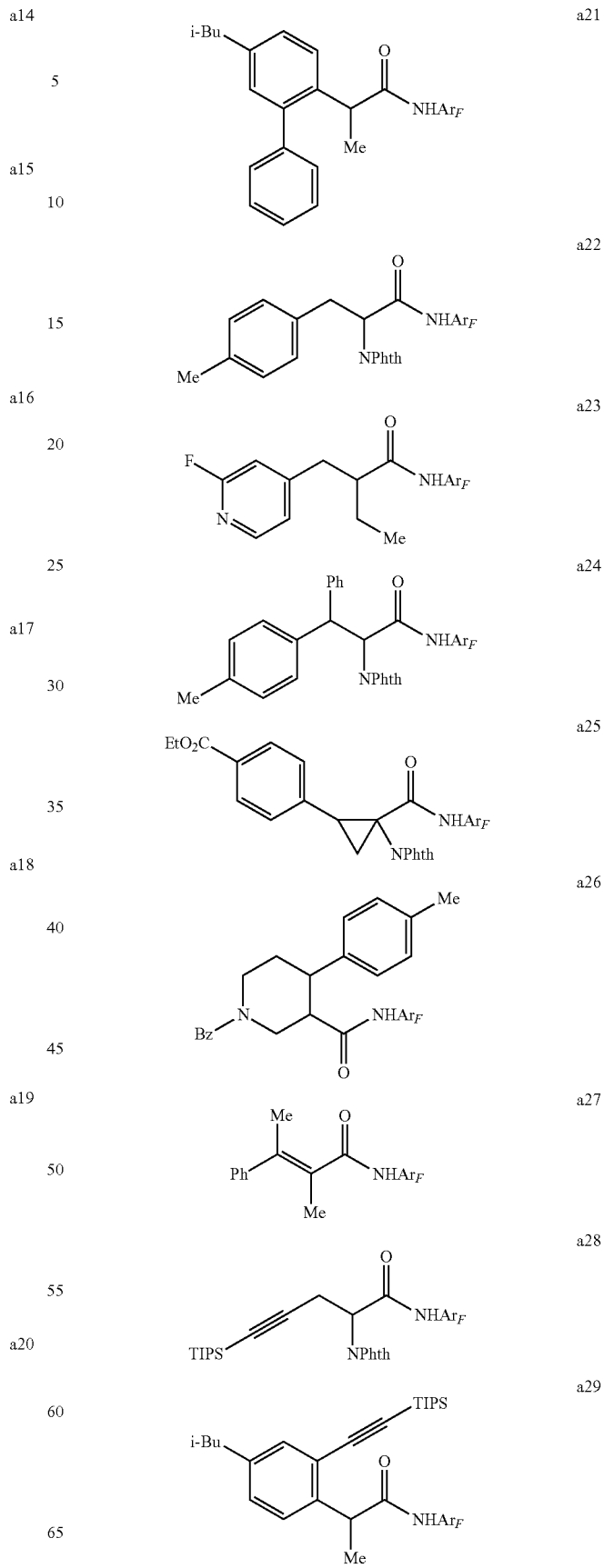

$Ar_F = p\text{-}C_6F_4CF_3$
The epoxy compounds are as follows:
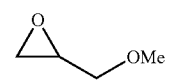 b1
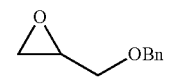 b2
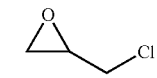 b3
 b4
 b5
 b6
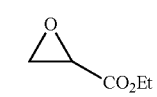 b7
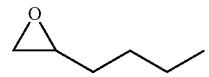 b8
The product structure is as follows:
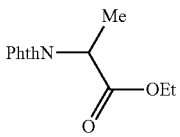 c1
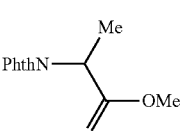 c2
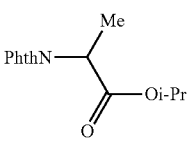 c3
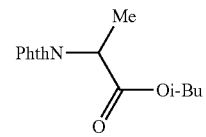 c4
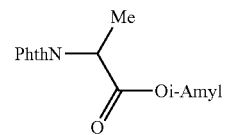 c5
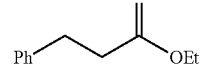 c6
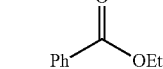 c7
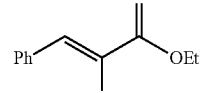 c8
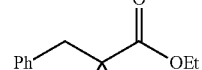 c9
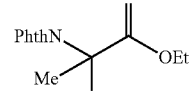 c10
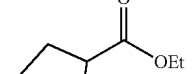 c11
 c12
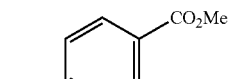 c13
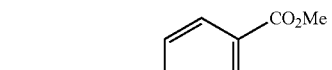 c14

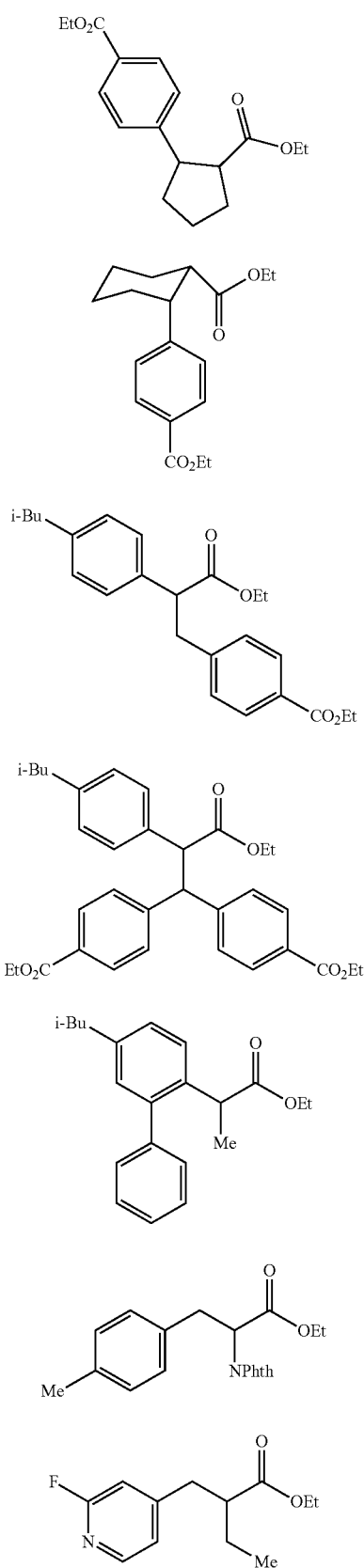

The reactants used in the following examples are as follows:

| | Amide-containing compound | Epoxy compound | pH adjuster | Solvent |
|---|---|---|---|---|
| Embodiments 1 to 2 | a1 | b1 | KOAc | absolute ethanol |
| Embodiments 3 to 10 | a1 | b1 | KOAc | absolute ethanol |
| EmbodimentEmbodiment 11 | a1 | b1 | CF$_3$CO$_2$K | absolute ethanol |
| Embodiment 12 | a1 | b1 | KHCO$_3$ | absolute ethanol |
| Embodiment 13 | a1 | b1 | K$_2$HPO$_4$ | absolute ethanol |
| Embodiment 14 | a1 | b1 | K$_2$CO$_3$ | absolute ethanol |
| Embodiment 15 | a1 | b1 | NaHCO$_3$ | absolute ethanol |
| Embodiment 16 | a1 | b1 | LiOH | absolute ethanol |
| Embodiment 17 | a1 | b1 | NaOAc | absolute ethanol |
| Embodiment 18 | a1 | b1 | KCl | absolute |

-continued

| | Amide-containing compound | Epoxy compound | pH adjuster | Solvent |
|---|---|---|---|---|
| Embodiment 19 | a1 | b1 | CF$_3$COONa | absolute ethanol |
| Embodiment 20 | a1 | b1 | CF$_3$COOK | absolute ethanol |
| Embodiment 21 | a1 | b1 | triethylamine | absolute ethanol |
| Embodiment 22 | a1 | b1 | KOAc | absolute ethanol |
| Embodiment 23 | a1 | b1 | KOAc | absolute ethanol |
| Embodiment 24 | a1 | b1 | KOAc | absolute ethanol |
| Embodiment 25 | a1 | b1 | KOAc | Methanol |
| Embodiment 26 | a1 | b1 | KOAc | Isopropanol |
| Embodiment 27 | a1 | b1 | KOAc | Isobutanol |
| Embodiment 28 | a1 | b1 | KOAc | Isoamyl alcohol |
| Embodiment 29 | a1 | b1 | KOAc | absolute ethanol |
| Embodiment 30 | a1 | b1 | KOAc | absolute ethanol |
| Embodiment 31 | a1 | b1 | KOAc | absolute ethanol |
| Embodiment 32 | a2 | b1 | KOAc | absolute ethanol |
| Embodiment 33 | a3 | b1 | KOAc | absolute ethanol |
| Embodiment 34 | a4 | b1 | KOAc | absolute ethanol |
| Embodiment 35 | a5 | b1 | KOAc | absolute ethanol |
| Embodiment 36 | a6 | b1 | KOAc | absolute ethanol |
| Embodiment 37 | a7 | b1 | KOAc | absolute ethanol |
| Embodiment 38 | a8 | b1 | KOAc | absolute ethanol |
| Embodiment 39 | a9 | b1 | KOAc | absolute ethanol |
| Embodiment 40 | a10 | b1 | KOAc | absolute ethanol |
| Embodiment 41 | a11 | b1 | KOAc | absolute ethanol |
| Embodiment 42 | a12 | b1 | KOAc | absolute ethanol |
| Embodiment 43 | a13 | b1 | KOAc | absolute ethanol |
| Embodiment 44 | a14 | b1 | KOAc | absolute methanol |
| Embodiment 45 | a15 | b1 | KOAc | absolute methanol |
| Embodiment 46 | a16 | b1 | KOAc | absolute methanol |
| Embodiment 47 | a17 | b1 | KOAc | absolute ethanol |
| Embodiment 48 | a18 | b1 | KOAc | absolute ethanol |
| Embodiment 49 | a19 | b1 | KOAc | absolute ethanol |
| Embodiment 50 | a20 | b1 | KOAc | absolute ethanol |
| Embodiment 51 | a21 | b1 | KOAc | absolute ethanol |
| Embodiment 52 | a22 | b1 | KOAc | absolute ethanol |
| Embodiment 53 | a23 | b1 | KOAc | absolute ethanol |
| Embodiment 54 | a24 | b1 | KOAc | absolute ethanol |
| Embodiment 55 | a25 | b1 | KOAc | absolute ethanol |
| Embodiment 56 | a26 | b1 | KOAc | absolute ethanol |
| Embodiment 57 | a27 | b1 | KOAc | absolute ethanol |
| Embodiment 58 | a28 | b1 | KOAc | absolute ethanol |
| Embodiment 59 | a29 | b1 | KOAc | absolute ethanol |
| Embodiment 60 | a1 | b2 | KOAc | absolute ethanol |
| Embodiment 61 | a1 | b3 | KOAc | absolute ethanol |
| Embodiment 62 | a1 | b4 | KOAc | absolute ethanol |
| Embodiment 63 | a1 | b5 | KOAc | absolute ethanol |
| Embodiment 64 | a1 | b6 | KOAc | absolute ethanol |
| Embodiment 65 | a1 | b7 | KOAc | absolute ethanol |
| Embodiment 66 | a1 | b8 | KOAc | absolute ethanol |

Embodiment 1 a1 (87.5 mg, 0.2 mmol), potassium acetate (19.6 mg, 0.2 mmol), absolute ethanol (2.0 mL, water <0.01 wt %), and methyl glycidyl ether b1 (52.9 mg, 0.6 mmol) are sequentially added to a 25 mL dry clean Schlenck tube with a magnetic stirrer to form a reaction system. The Schlenck tube is heated in a 90° C. oil bath for 35 hours, and TLC shows that the raw material is completely reacted to obtain a product system. The product system is stopped heating and cooled to a room temperature, and the solvent is removed under reduced pressure to give a residue, and then 2.0 mL of purified water is added to the residue to form a mixture; the mixture is stirred, adjusted to pH 4 with 3M hydrochloric acid, and then extracted with n-hexane (3 mL×3) to obtain an organic phase; the combined organic phase is dried with anhydrous sodium sulfate, filtered after drying; the filtrate is concentrated to obtain 45.5 mg of pure product, with a yield of 92%.

The chemical reaction of the above alcoholysis process is as follows:

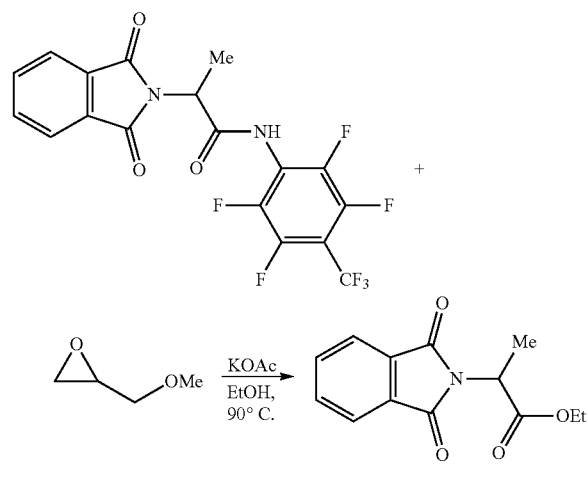 [SMILES: CC(C(=O)Nc1c(F)c(F)c(C(F)(F)F)c(F)c1F)N1C(=O)c2ccccc2C1=O ; COCC1CO1 ; CCOC(=O)C(C)N1C(=O)c2ccccc2C1=O ; "KOAc"]

Nuclear Magnetic Test Results of Product c1 (Ethyl 2-(1,3-dioxoisoindolin-2-yl)propanoate)

$^1$NMR (400 MHz, CDCl$_3$) δ 7.92-7.79 (m, 2H), 7.77-7.60 (m, 2H), 4.95 (q, J=7.5 Hz, 1H), 4.19 (td, J=7.0, 3.5 Hz, 2H), 1.69 (d, J=7.5 Hz, 3H), 1.22 (t, J=7.0 Hz, 3H). $^{13}$C NMR (125 MHz, CDCl$_3$) δ 169.75, 167.47, 134.20, 131.99, 123.49, 61.90, 47.66, 15.28, 14.12.

Embodiment 2

It differs from Embodiment 1 in that after the amount of each material in Embodiment 1 is increased by 100 times, an alcoholysis reaction is carried out by using a 500 mL pressure reactor, and the filtrate is concentrated to obtain a pure product of 4.648 g, with a yield of 94%. The yield of Embodiment 2 is higher than that of Embodiment 1, because the adhesion loss is large in the operation of small-amount reaction of Embodiment 1, and the yield in large-amount reaction is more accurate.

Embodiment 3

It differs from Embodiment 1 in that the molar ratio of methyl glycidyl ether b1 to a1 is 5:1, and the yield is 93%.

Embodiment 4

It differs from Embodiment 1 in that the molar ratio of methyl glycidyl ether b1 to a1 is 1:1, and the yield is 69%.

Embodiment 5

It differs from Embodiment 1 in that the molar ratio of methyl glycidyl ether b1 to a1 is 8:1, and the yield is 94%.

Embodiment 6

It differs from Embodiment 1 in that the Schlenck tube is heated in an oil bath at 80° C. for 35 hours, and the product yield is 84%.

Embodiment 7

It differs from Embodiment 1 in that the Schlenck tube is heated in an oil bath at 100° C. for 35 hours, and the product yield is 91%.

Embodiment 8

It differs from Embodiment 1 in that the Schlenck tube is heated in an oil bath at 150° C. for 35 hours, and the product yield is 82%.

Embodiment 9

It differs from Embodiment 1 in that the Schlenck tube is heated in an oil bath at 50° C. for 35 hours, and the product yield is 48%.

Embodiment 10

It differs from Embodiment 1 in that the Schlenck tube is heated in an oil bath at 165° C. for 35 hours, and the product yield is 74%.

Embodiment 11

It differs from Embodiment 1 in that the pH adjuster used is CF3CO2K, and the product yield is 93%.

Embodiment 12

It differs from Embodiment 1 in that the pH adjuster used is KHCO$_3$, and the product yield is 74%.

Embodiment 13

It differs from Embodiment 1 in that the pH adjuster used is K$_2$HPO$_4$, and the product yield is 51%.

Embodiment 14

It differs from Embodiment 1 in that the pH adjuster used is K$_2$CO$_3$, and the product yield is 22%.

Embodiment 15 a1 (87.5 mg, 0.2 mmol), NaHCO$_3$ (16.8 mg, 0.2 mmol), absolute ethanol (2.0 mL, water ≤0.01 wt %), and methyl glycidyl ether b1 (52.9 mg, 0.6 mmol) are sequentially added to a 25 mL dry clean Schlenck tube with a magnetic stirrer to form a reaction system. The Schlenck tube is heated in a 90° C. oil bath for 35 hours, and TLC shows that the raw material is completely reacted to obtain a product system. The product system is stopped heating and cooled to a room temperature, and the solvent is removed under reduced pressure to give a residue, the residue is purified by silica gel column chromatography (hexane/EA=15/1) to obtain a pure product of 36.1 mg, with a yield of 73%.

Embodiment 16 a1 (86.8 mg, 0.2 mmol), LiOH (4.8 mg, 0.2 mmol), absolute ethanol (2.0 mL, water ≤0.01 wt %), and methyl glycidyl ether b1 (52.9 mg, 0.6 mmol) are sequentially added to a 25 mL dry clean Schlenck tube with a magnetic stirrer to form a reaction system. The Schlenck tube is heated in a 90° C. oil bath for 35 hours, and TLC shows that the raw material is completely reacted to obtain a product system. The product system is stopped heating and cooled to a room temperature, and the solvent is removed under reduced pressure to give a residue, the residue is purified by silica gel column chromatography (hexane/EA=15/1) to obtain a pure product of 32.1 mg, with a yield of 65%. The pH adjuster used in this embodiment is LiOH, which is a strong base, not only adjusts pH value in the reaction, but also acts as a metal ion for complexation activation.

Embodiment 17 a1 (86.8 mg, 0.2 mmol), NaOAc (16.4 mg, 0.2 mmol), absolute ethanol (2.0 mL, water ≤0.01 wt %), and methyl glycidyl ether b1 (52.9 mg, 0.6 mmol) are sequentially added to a 25 mL dry clean Schlenck tube with a magnetic stirrer to form a reaction system. The Schlenck tube is heated in a 90° C. oil bath for 35 hours, and TLC shows that the raw material is completely reacted to obtain a product system. The product system is stopped heating and cooled to a room temperature, and the solvent is removed under reduced pressure to give a residue, the residue is purified by silica gel column chromatography (hexane/EA=15/1) to obtain a pure product of 43.0 mg, with a yield of 87%.

Embodiment 18 a1 (86.8 mg, 0.2 mmol), KCl (14.9 mg, 0.2 mmol), absolute ethanol (2.0 mL, water ≤0.01 wt %), and methyl glycidyl ether b1 (52.9 mg, 0.6 mmol) are sequentially added to a 25 mL dry clean Schlenck tube with a magnetic stirrer to form a reaction system. The Schlenck tube is heated in a 90° C. oil bath for 35 hours, and TLC shows that the raw material is completely reacted to obtain a product system. The product system is stopped heating and cooled to a room temperature, and the solvent is removed under reduced pressure to give a residue, the residue is purified by silica gel column chromatography (hexane/EA=15/1) to obtain a pure product of 15.3 mg, with a yield of 31%.

Embodiment 19 a1 (86.8 mg, 0.2 mmol), sodium trifluoroacetate (27.2 mg, 0.2 mmol), absolute ethanol (2.0 mL, water ≤0.01 wt %), and methyl glycidyl ether b1 (52.9 mg, 0.6 mmol) are sequentially added to a 25 mL dry clean Schlenck tube with a magnetic stirrer to form a reaction system. The Schlenck tube is heated in a 90° C. oil bath for 45 hours, and TLC shows that the raw material is completely reacted to obtain a product system. The product system is stopped heating and cooled to a room temperature, and the solvent is removed under reduced pressure to give a residue, the residue is purified by silica gel column chromatography (hexane/EA=15/1) to obtain a pure product of 46.0 mg, with a yield of 93%.

Embodiment 20 a1 (86.8 mg, 0.2 mmol), potassium trifluoroacetate (30.4 mg, 0.2 mmol), absolute ethanol (2.0 mL, water ≤0.01 wt %), and methyl glycidyl ether b1 (52.9 mg, 0.6 mmol) are sequentially added to a 25 mL dry clean Schlenck tube with a magnetic stirrer to form a reaction system. The Schlenck tube is heated in a 90° C. oil bath for 45 hours, and TLC shows that the raw material is completely reacted to obtain a product system. The product system is stopped heating and cooled to a room temperature, and the solvent is removed under reduced pressure to give a residue, the residue is purified by silica gel column chromatography (hexane/EA=15/1) to obtain a pure product of 47.0 mg, with a yield of 95%. Although the yield is slightly increased, the reaction time is prolonged, and the potassium trifluoroacetate is more expensive than potassium acetate.

Embodiment 21 a1 (86.8 mg, 0.2 mmol), triethylamine (20.2 mg, 0.2 mmol), absolute ethanol (2.0 mL, water ≤0.01 wt %), and methyl glycidyl ether b1 (52.9 mg, 0.6 mmol) are sequentially added to a 25 mL dry clean Schlenck tube with a magnetic stirrer to form a reaction system. The Schlenck tube is heated in a 90° C. oil bath for 35 hours, and TLC shows that the raw material is completely reacted to obtain a product system. The product system is stopped heating and cooled to a room temperature, and the solvent is removed under reduced pressure to give a residue, the residue is purified by silica gel column chromatography (hexane/EA=15/1) to obtain a pure product of 35.6 mg, with a yield of 72%.

Embodiment 22 a1 (86.8 mg, 0.2 mmol), potassium acetate (19.6 mg, 0.2 mmol), absolute ethanol (1.0 mL, water ≤0.01 wt %), and methyl glycidyl ether b1 (52.9 mg, 0.6 mmol) are sequentially added to a 25 mL dry clean Schlenck tube with a magnetic stirrer to form a reaction system. The Schlenck tube is heated in a 90° C. oil bath for 35 hours, and TLC shows that the raw material is completely reacted to obtain a product system. The product system is stopped heating and cooled to a room temperature, and the solvent is removed under reduced pressure to give a residue, the residue is purified by silica gel column chromatography (hexane/EA=15/1) to obtain a pure product of 38.6 mg, with a yield of 78%.

Embodiment 23 a1 (86.8 mg, 0.2 mmol), potassium acetate (19.6 mg, 0.2 mmol), absolute ethanol (3.0 mL, water ≤0.01 wt %), and methyl glycidyl ether b1 (52.9 mg, 0.6 mmol) are sequentially added to a 25 mL dry clean Schlenck tube with a magnetic stirrer to form a reaction system. The Schlenck tube is heated in a 90° C. oil bath for 35 hours, and TLC shows that the raw material is completely reacted to obtain a product system. The product system is stopped heating and cooled to a room temperature, and the solvent is removed under reduced pressure to give a residue, the residue is purified by silica gel column chromatography (hexane/EA=15/1) to obtain a pure product of 44.0 mg, with a yield of 89%.

Embodiment 24 a1 (86.8 mg, 0.2 mmol), potassium acetate (19.6 mg, 0.2 mmol), absolute ethanol (4.0 mL, water ≤0.01 wt %), and methyl glycidyl ether b1 (52.9 mg, 0.6 mmol) are sequentially added to a 25 mL dry clean Schlenck tube with a magnetic stirrer to form a reaction system. The Schlenck tube is heated in a 90° C. oil bath for 35 hours, and TLC shows that the raw material is completely reacted to obtain a product system. The product system is stopped heating and cooled to a room temperature, and the solvent is removed under reduced pressure to give a residue, the residue is purified by silica gel column chromatography (hexane/EA=15/1) to obtain a pure product of 20.3 mg, with a yield of 41%.

Embodiment 25

It differs from Embodiment 1 in that the solvent used is methanol, and the product yield is 91%.

Nuclear Magnetic Test Results of Product c2
(Methyl 2-(1,3-dioxoisoindolin-2-yl) propanoate)

$^1$NMR (400 MHz, CDCl$_3$) δ 7.82-7.75 (m, 2H), 7.72-7.65 (m, 2H), 4.91 (q, J=7.5 Hz, 1H), 3.67 (s, 3H), 1.63 (d, J=7.5 Hz, 3H).

Embodiment 26

It differs from Embodiment 1 in that the solvent used is isopropanol, and the product yield is 95%.

Nuclear Magnetic Test Results of Product c3
(Isopropyl 2-(1,3-dioxoisoindolin-2-yl) propanoate)

$^1$NMR (400 MHz, CDCl$_3$) δ 7.83-7.76 (m, 2H), 7.72-7.66 (m, 2H), 5.09-4.95 (m, 1H), 4.87 (q, J=7.5 Hz, 1H), 1.63 (d, J=7.5 Hz, 1H), 1.16 (dd, J=20.0, 6.5 Hz, 6H).

Embodiment 27

It differs from Embodiment 1 in that the solvent used is isobutanol, and the product yield is 92%.

Nuclear Magnetic Test Results of Product c4
(Isobutyl 2-(1,3-dioxoisoindolin-2-yl) propanoate)

$^1$NMR (400 MHz, CDCl$_3$) δ 7.83-7.76 (m, 2H), 7.73-7.65 (m, 2H), 4.94 (q, J=7.5 Hz, 1H), 3.93-3.83 (m, 2H), 1.90-1.77 (m, 1H), 1.67 (d, J=7.5 Hz, 3H), 0.81 (d, J=7.0 Hz, 6H).

Embodiment 28

It differs from Embodiment 1 in that the solvent used is isoamyl alcohol, and the product yield is 87%.

Nuclear Magnetic Test Results of Product c5
(Isopentyl 2-(1,3-dioxoisoindolin-2-yl) propanoate)

$^1$NMR (400 MHz, CDCl$_3$) δ 7.85-7.80 (m, 2H), 7.74-7.67 (m, 2H), 4.98-4.89 (m, 1H), 4.14 (t, J=7.0 Hz, 2H), 1.67 (d, J=7.5 Hz, 3H), 1.59-7.50 (m, 1H), 1.49-1.37 (m, 2H), 0.84-0.75 (m, 6H).

Embodiment 29

It differs from Embodiment 1 in that the product system is stopped heating and cooled to a room temperature, and the solvent is removed under reduced pressure to give a residue, and then 2.0 mL of purified water is added to the residue to form a mixture; the mixture is stirred, adjusted to pH 3.5 with 3M hydrochloric acid, and then extracted with n-hexane (3 mL×3) to obtain an organic phase; the combined organic phase is dried with anhydrous sodium sulfate, filtered after drying, with a yield of 91%.

Embodiment 30

It differs from Embodiment 1 in that the product system is stopped heating and cooled to a room temperature, and the solvent is removed under reduced pressure to give a residue, and then 2.0 mL of purified water is added to the residue to form a mixture; the mixture is stirred, adjusted to pH 4.5 with 3M hydrochloric acid, and then extracted with n-hexane (3 mL×3) to obtain an organic phase; the combined organic phase is dried with anhydrous sodium sulfate, filtered after drying, with a yield of 89%.

Embodiment 31

It differs from Embodiment 1 in that the product system is stopped heating and cooled to a room temperature, and the solvent is removed under reduced pressure to give a residue, and then 2.0 mL of purified water is added to the residue to form a mixture; the mixture is stirred, adjusted to pH 5 with 3M hydrochloric acid, and then extracted with n-hexane (3 mL×3) to obtain an organic phase; the combined organic phase is dried with anhydrous sodium sulfate, filtered after drying, with a yield of 84%.

Embodiment 32

It differs from Embodiment 1 in that the amide compound used is a2, and the yield is 96%.

Nuclear Magnetic Test Results of Product c6 (Ethyl 3-phenylpropanoate)

$a^8$NMR (500 MHz, CDCl$_3$) δ 7.32-7.26 (m, 2H), 7.24-7.17 (m, 3H), 4.13 (q, J=7.0 Hz, 2H), 2.96 (t, J=8.0 Hz, 2H), 2.63 (t, J=8.0 Hz, 2H), 1.24 (t, J=7.0 Hz, 3H).

Embodiment 33

It differs from Embodiment 1 in that the amide compound used is a3, and the yield is 41%.

Embodiment 34

It differs from Embodiment 1 in that the amide compound used is a4, and the yield is 97%.

Embodiment 35

It differs from Embodiment 1 in that the amide compound used is a5, and the yield is 96%.

Embodiment 36

It differs from Embodiment 1 in that the amide compound used is a6, and the yield is 93%.

Embodiment 37

It differs from Embodiment 1 in that the amide compound used is a7, and the yield is 90%.

Embodiment 38

It differs from Embodiment 1 in that the amide compound used is a8, and the yield is 62%.

Nuclear Magnetic Test Results of Product c7 (Ethyl benzoate)

$^1$H NMR (500 MHz, CDCl$_3$) δ 8.13-7.97 (m, 2H), 7.58-7.53 (m, 1H), 7.47-7.38 (m, 2H), 4.39 (q, J=7.0 Hz, 2H), 1.42 (t, J=7.0 Hz, 3H).

Embodiment 39

It differs from Embodiment 1 in that the amide compound used is a9, and the yield is 91%.

Nuclear Magnetic Test Results of Product c8 (Ethyl 2-methyl-3-phenylacrylate)

$^1$H NMR (500 MHz, CDCl$_3$) δ 7.70 (s, 1H), 7.43-7.36 (m, 4H), 7.35-7.29 (m, 1H), 4.28 (q, J=7.0 Hz, 2H), 2.13 (s, 3H), 1.36 (t, J=7.0 Hz, 3H).

Embodiment 40

It differs from Embodiment 1 in that the amide compound used is a10, and the yield is 97%.

Embodiment 41

It differs from Embodiment 1 in that the amide compound used is a11, and the yield is 94%.

Nuclear Magnetic Test Results of Product c9 (Ethyl 2,2-dimethyl-3-phenylpropanoate)

$^1$H NMR (500 MHz, CDCl$_3$) δ 7.30-7.27 (m, 2H), 7.25-7.20 (m, a8), 7.13 (d, J=7.0 Hz, 2H), 4.13 (q, J=7.0 Hz, 2H), 2.87 (s, 2H), 1.25 (t, J=7.0 Hz, 4H), 1.19 (s, 6H). $^{13}$C NMR (125 MHz, CDCl$_3$) δ 177.62, 138.10, 130.30, 128.06, 126.52, 60.52, 46.41, 43.61, 25.09, 14.31.

Embodiment 42

It differs from Embodiment 1 in that the amide compound used is a12, and the yield is 90%.

Nuclear Magnetic Test Results of Product c10 (Ethyl 2,2-dimethyl-3-phenylpropanoate)

1NMR (400 MHz, CDCl$_3$) δ 7.85-7.75 (m, 2H), 7.74-7.67 (m, 2H), 4.22 (q, J=7.0 Hz, 2H), 1.83 (s, 6H), 1.25 (t, J=7.0 Hz, 3H).

Embodiment 43

It differs from Embodiment 1 in that the amide compound used is a13, and the yield is 89%.

Nuclear Magnetic Test Results of Product c11 (Ethyl 1-benzoylpyrrolidine-2-carboxylate)

$^1$H NMR (500 MHz, CDCl$_3$) δ 7.55 (d, J=6.5 Hz, 2H), 7.43-7.35 (m, 3H), 4.69-4.59 (m, 1H), 4.22 (q, J=7.0 Hz, 2H), 3.64 (dt, J=14.0, 7.0 Hz, 1H), 3.56-3.47 (m, 1H), 2.31 (dd, J=14.0, 7.0 Hz, 1H), 2.04-1.97 (m, 2H), 1.92-1.82 (m, 1H), 1.29 (t, J=7.0 Hz, 3H).

The ArF in the structural formulas of the following Embodiments 44 to 59 is p-CF$_3$C$_5$F$_4$, and each of the amide-containing compounds can be obtained by using a commodity existing in the prior art or by subjecting the corresponding substrate to CH activation. The product system arising from the CH activation can be directly subjected to the amide alcoholysis of the following Embodiments without purification.

Embodiment 44 a14 (87.06 mg, 0.2 mmol), potassium acetate (19.6 mg, 0.2 mmol), anhydrous methanol (2.0 mL, water ≤0.01 wt %), and methyl glycidyl ether b1 (52.9 mg, 0.6 mmol) are sequentially added to a 25 mL dry clean Schlenck tube with a magnetic stirrer to form a reaction system. The Schlenck tube is heated in a 90° C. oil bath for 35 hours, and TLC shows that the raw material is completely reacted to obtain a product system. The product system is stopped heating and cooled to a room temperature, and the solvent is removed under reduced pressure to give a residue, the residue is purified by silica gel column chromatography (hexane/EA=10/1) to obtain a pure product of 42.3 mg, with a yield of 90%.

Nuclear Magnetic Test Results of Product c12 (Methyl 4-(2-(methoxycarbonyl) cyclopropyl) benzoate)

$^1$NMR (400 MHz, CDCl$_3$) δ 7.94 (d, J=8.0 Hz, 2H), 7.33 (d, J=8.0 Hz, 2H), 3.89 (s, 3H), 3.43 (s, 3H), 2.60 (q, J=8.0 Hz, 1H), 2.18-2.13 (m, 1H), 1.77-1.72 (m, 1H), 1.43-1.37 (m, 1H).

Embodiment 45 a15 (89.86 mg, 0.2 mmol), potassium acetate (19.6 mg, 0.2 mmol), anhydrous methanol (2.0 mL, water ≤0.01 wt %), and methyl glycidyl ether b1 (52.9 mg, 0.6 mmol) are sequentially added to a 25 mL dry clean Schlenck tube with a magnetic stirrer to form a reaction system. The Schlenck tube is heated in a 90° C. oil bath for 35 hours, and TLC shows that the raw material is completely reacted to obtain a product system. The product system is stopped heating and cooled to a room temperature, and the solvent is removed under reduced pressure to give a residue, the residue is purified by silica gel column chromatography (hexane/EA=10/1) to obtain a pure product, with a yield of 93%.

Nuclear Magnetic Test Results of Product c13 (Methyl 4-(2-(methoxycarbonyl) cyclobutyl) benzoate)

$^1$H NMR (400 MHz, CDCl$_3$) δ 7.98 (d, J=8.0 Hz, 2H), 7.31 (d, J=8.0 Hz, 2H), 3.91 (s, 3H), 3.88-3.81 (m, 1H), 3.71 (s, 3H), 3.22 (q, J=8.0 Hz, 1H), 2.38-2.31 (m, 2H), 2.29-2.12 (m, 2H). $^{13}$C NMR (125 MHz, CDCl$_3$) δ 174.66, 167.13, 148.93, 129.86, 128.39, 126.50, 52.16, 51.94, 45.07, 43.10, 25.33, 21.90.

Embodiment 46 a16 (105.08 mg, 0.2 mmol), potassium acetate (19.6 mg, 0.2 mmol), anhydrous methanol (2.0 mL, water ≤0.01 wt %), and methyl glycidyl ether b1 (52.9 mg, 0.6 mmol) are sequentially added to a 25 mL dry clean Schlenck tube with a magnetic stirrer to form a reaction system. The Schlenck tube is heated in a 90° C. oil bath for 35 hours, and TLC shows that the raw material is completely reacted to obtain a product system. The product system is stopped heating and cooled to a room temperature, and the solvent is removed under reduced pressure to give a residue, the residue is purified by silica gel column chromatography (hexane/EA=10/1) to obtain a pure product, with a yield of 95%.

Nuclear Magnetic Test Results of Product c14 (Dimethyl 4,4'-(2-(methoxycarbonyl) cyclobutane-1,3-diyl) dibenzoate)

$^1$H NMR (400 MHz, CDCl$_3$) δ 8.00 (d, J=8.0 Hz, 4H), 7.34 (d, J=8.0 Hz, 4H), 3.91 (s, 6H), 3.84 (q, J=8.0 Hz, 2H), 3.75 (s, 3H), 3.32-3.28 (m, 1H), 2.87-2.81 (m, 1H), 2.34-2.26 (m, 1H). $^{13}$C NMR (125 MHz, CDCl$_3$) δ 173.61, 167.04, 147.96, 130.01, 128.73, 126.67, 52.26, 52.23, 51.98, 39.53, 32.49, 29.85.

Embodiment 47 a17 (95.47 mg, 0.2 mmol), potassium acetate (19.6 mg, 0.2 mmol), absolute ethanol (2.0 mL, water ≤0.01 wt %), and methyl glycidyl ether b1 (52.9 mg, 0.6 mmol) are sequentially added to a 25 mL dry clean Schlenck tube with a magnetic stirrer to form a reaction system. The Schlenck tube is heated in a 90° C. oil bath for 35 hours, and TLC shows that the raw material is completely reacted to obtain a product system. The product system is stopped heating and cooled to a room temperature, and the solvent is removed under reduced pressure to give a residue, the residue is purified by silica gel column chromatography (hexane/EA=10/1) to obtain a pure product of 53.8 mg, with a yield of 93%.

Nuclear Magnetic Test Results of Product c15
(Ethyl 4-(2-(ethoxycarbonyl) cyclopentyl) benzoate)

$^1$H NMR (500 MHz, CDCl$_3$) δ 7.96 (t, J=8.0 Hz, 2H), 7.29 (d, J=8.0 Hz, 2H), 4.35 (q, J=7.0 Hz, 2H), 4.05 (q, J=7.0 Hz, 2H), 3.37 (q, J=9.0 Hz, 1H), 2.81 (q, J=9.0 Hz, 1H), 2.24-2.10 (m, 2H), 2.02-1.93 (m, 1H), 1.91-1.79 (m, 1H), 1.79-1.69 (m, 1H), 1.37 (t, J=7.0 Hz, 3H), 1.14 (t, J=7.0 Hz, 3H). $^{13}$C NMR (125 MHz, CDCl$_3$) δ 175.54, 166.67, 149.47, 129.83, 128.74, 127.34, 60.90, 60.50, 52.18, 49.86, 35.08, 30.84, 25.16, 14.47, 14.31.

Embodiment 48 a18 (98.28 mg, 0.2 mmol), potassium acetate (19.6 mg, 0.2 mmol), absolute ethanol (2.0 mL, water ≤0.01 wt %), and methyl glycidyl ether b1 (52.9 mg, 0.6 mmol) are sequentially added to a 25 mL dry clean Schlenck tube with a magnetic stirrer to form a reaction system. The Schlenck tube is heated in a 90° C. oil bath for 35 hours, and TLC shows that the raw material is completely reacted to obtain a product system. The product system is stopped heating and cooled to a room temperature, and the solvent is removed under reduced pressure to give a residue, the residue is purified by silica gel column chromatography (hexane/EA=10/1) to obtain a pure product of 54.1 mg, with a yield of 89%.

Nuclear Magnetic Test Results of Product c16
(Ethyl 4-(2-(ethoxycarbonyl) cyclohexyl) benzoate $^1$H NMR (500 MHz, CDCl$_3$) δ 7.94 (d, J=8.0 Hz, 2H), 7.26 (d, J=8.0 Hz, 2H), 4.35 (q, J=7.0 Hz, 2H), 3.90-3.80 (m, 2H), 2.89-2.76 (m, 1H), 2.63-2.53 (m, 1H), 2.08-1.99 (m, 1H), 1.92-1.78 (m, 3H), 1.62-1.56 (m, 1H), 1.50-1.42 (m, 2H), 1.42-1.34 (m, 4H), 0.94 (t, J=7.0 Hz, 3H). $^{13}$C NMR (125 MHz, CDCl$_3$) δ 174.95, 166.72, 150.21, 129.75, 128.74, 127.49, 60.90, 60.09, 49.97, 46.82, 34.18, 30.17, 26.19, 25.42, 14.47, 14.10.

Embodiment 49 a19 (113.90 mg, 0.2 mmol), potassium acetate (19.6 mg, 0.2 mmol), absolute ethanol (2.0 mL, water ≤0.01 wt %), and methyl glycidyl ether b1 (52.9 mg, 0.6 mmol) are sequentially added to a 25 mL dry clean Schlenck tube with a magnetic stirrer to form a reaction system. The Schlenck tube is heated in a 90° C. oil bath for 35 hours, and TLC shows that the raw material is completely reacted to obtain a product system. The product system is stopped heating and cooled to a room temperature, and the solvent is removed under reduced pressure to give a residue, the residue is purified by silica gel column chromatography (hexane/EA=25/1) to obtain a pure product, with a yield of 95%.

Nuclear Magnetic Test Results of Product c17
(Ethyl 4-(3-ethoxy-2-(4-isobutylphenyl)-3-oxopropyl) benzoate)

$^1$H NMR (400 MHz, CDCl$_3$) δ 7.91 (d, J=8.0 Hz, 2H), 7.21-7.17 (m, 4H), 7.08 (d, J=8.0 Hz, 2H), 4.35 (q, J=8.0 Hz, 2H), 4.15-3.96 (m, 2H), 3.83-3.76 (m, 1H), 3.46-3.41 (m, 1H), 3.08-3.03 (m, 1H), 2.44 (d, J=8.0 Hz, 2H), 1.89-1.79 (m, 1H), 1.38 (t, J=8.0 Hz, 3H), 1.12 (t, J=8.0 Hz, 3H), 0.89 (d, J=8.0 Hz, 6H). $^{13}$C NMR (125 MHz, CDCl$_3$) δ 173.30, 166.65, 144.65, 141.00, 135.66, 129.63, 129.47, 129.08, 128.70, 127.65, 60.91, 53.05, 45.11, 39.95, 30.26, 22.44, 14.42, 14.14.

Embodiment 50 a20 (143.53 mg, 0.2 mmol), potassium acetate (19.6 mg, 0.2 mmol), absolute ethanol (2.0 mL, water ≤0.01 wt %), and methyl glycidyl ether b1 (52.9 mg, 0.6 mmol) are sequentially added to a 25 mL dry clean Schlenck tube with a magnetic stirrer to form a reaction system. The Schlenck tube is heated in a 90° C. oil bath for 35 hours, and TLC shows that the raw material is completely reacted to obtain a product system. The product system is stopped heating and cooled to a room temperature, and the solvent is removed under reduced pressure to give a residue, the residue is purified by silica gel column chromatography (hexane/EA=25/1) to obtain a pure product, with a yield of 96%.

Nuclear Magnetic Test Results of Product c18 (Diethyl 4,4'-(3-ethoxy-2-(4-isobutylphenyl)-3-oxopropane-1,1-diyl) dibenzoate)

$^1$H NMR (500 MHz, CDCl$_3$) δ 7.99 (d, J=8.0 Hz, 2H), 7.73 (d, J=8.0 Hz, 2H), 7.48 (d, J=8.0 Hz, 2H), 7.15 (d, J=8.0 Hz, 2H), 7.06 (d, J=8.0 Hz, 2H), 6.94 (d, J=8.0 Hz, 2H), 4.79 (d, J=12.0 Hz, 1H), 4.40-4.33 (m, 3H), 4.27 (q, J=7.0 Hz, 2H), 4.02-3.96 (m, 1H), 3.94-3.88 (m, 1H), 2.35 (d, J=7.0 Hz, 2H), 1.79-1.73 (m, 1H), 1.37 (t, J=7.0 Hz, 3H), 1.31 (t, J=7.0 Hz, 3H), 1.01 (t, J=7.0 Hz, 3H), 0.82-0.80 (m, 6H).

Embodiment 51 a21 (99.49 mg, 0.2 mmol), potassium acetate (19.6 mg, 0.2 mmol), absolute ethanol (2.0 mL, water ≤0.01 wt %), and methyl glycidyl ether b1 (52.9 mg, 0.6 mmol) are sequentially added to a 25 mL dry clean Schlenck tube with a magnetic stirrer to form a reaction system. The Schlenck tube is heated in a 90° C. oil bath for 35 hours, and TLC shows that the raw material is completely reacted to obtain a product system. The product system is stopped heating and cooled to a room temperature, and the solvent is removed under reduced pressure to give a residue, the residue is purified by silica gel column chromatography (hexane/EA=50/1) to obtain a pure product, with a yield of 96%.

Nuclear Magnetic Test Results of Product c19
(Ethyl 2-(5-isobutylbiphenyl-2-yl) propanoate)

$^1$H NMR (500 MHz, CDCl$_3$) δ 7.47-7.40 (m, 2H), 7.36 (m, 4H), 7.15 (d, J=8.0 Hz, 1H), 7.04 (s, 1H), 4.17-4.05 (m, 2H), 3.87 (q, J=7.0 Hz, 1H), 2.49 (d, J=7.0 Hz, 2H), 1.94-1.86 (m, 1H), 1.37 (d, J=7.0 Hz, 3H), 1.20 (t, J=7.0 Hz, 3H), 0.94 (d, J=6.5 Hz, 6H). $^{13}$C NMR (125 MHz, CDCl$_3$) δ 175.21, 141.65, 141.51, 140.05, 136.04, 130.96, 129.59, 128.68, 128.16, 127.04, 126.62, 60.63, 45.12, 41.02, 30.23, 22.57, 22.55, 19.39, 14.20.

Embodiment 52 a22 (104.88 mg, 0.2 mmol), potassium acetate (19.6 mg, 0.2 mmol), absolute ethanol (2.0 mL, water ≤0.01 wt %), and methyl glycidyl ether b1 (52.9 mg, 0.6 mmol) are sequentially added to a 25 mL dry clean Schlenck tube with a magnetic stirrer to form a reaction system. The Schlenck tube is heated in a 90° C. oil bath for 35 hours, and TLC shows that the raw material is completely reacted to obtain a product system. The product system is stopped heating and cooled to a room temperature, and the solvent is removed under reduced pressure to give a residue, the residue is purified by silica gel column chromatography (hexane/EA=15/1) to obtain a pure product, with a yield of 93%.

Nuclear Magnetic Test Results of Product c20 (Ethyl 2-(1,3-dioxoisoindolin-2-yl)-3-p-tolylpropanoate)

$^1$H NMR (500 MHz, CDCl$_3$) δ 7.82-7.74 (m, 2H), 7.71-7.63 (m, 2H), 7.04 (d, J=8.0 Hz, 2H), 6.98 (d, J=8.0 Hz, 2H), 5.15-5.08 (m, 1H), 4.27-4.20 (m, 2H), 3.58-3.46 (m, 2H), 2.22 (s, 3H), 1.25 (t, J=7.0 Hz, 3H).

Embodiment 53 a23 (82.46 mg, 0.2 mmol), potassium acetate (19.6 mg, 0.2 mmol), absolute ethanol (2.0 mL, water ≤0.01 wt %), and methyl glycidyl ether b1 (52.9 mg, 0.6 mmol) are sequentially added to a 25 mL dry clean Schlenck tube with a magnetic stirrer to form a reaction system. The Schlenck tube is heated in a 90° C. oil bath for 35 hours, and TLC shows that the raw material is completely reacted to obtain a product system. The product system is stopped heating and cooled to a room temperature, and the solvent is removed under reduced pressure to give a residue, the residue is purified by silica gel column chromatography (hexane/EA=15/1) to obtain a pure product, with a yield of 94%.

Nuclear Magnetic Test Results of Product c21 (Ethyl 2-((2-fluoropyridin-4-yl) methyl) butanoate)

1H NMR (500 MHz, CDCl$_3$) δ 8.09 (d, J=5.0 Hz, 1H), 6.99 (d, J=5.0 Hz, 1H), 6.74 (s, 1H), 4.15-4.01 (m, 2H), 2.96 (dd, J=14.0, 9.5 Hz, 1H), 2.77 (dd, J=14.0, 6.0 Hz, 1H), 2.65-2.55 (m, 1H), 1.72-1.65 (m, 1H), 1.63-1.53 (m, 1H), 1.16 (t, J=7.0 Hz, 3H), 0.94 (t, J=7.5 Hz, 3H). $^{13}$C NMR (125 MHz, CDCl$_3$) b 174.66, 164.15 (d, J=237.5 Hz, 1H), 154.76 (d, J=7.5 Hz, 1H), 147.57 (d, J=15.0 Hz, 1H), 122.07 (d, J=3.8 Hz, 1H), 109.75 (d, J=36.3 Hz, 1H), 60.65, 48.01, 37.14 (d, J=2.5 Hz, 1H), 25.63, 14.33, 11.66. $^{19}$F NMR (400 MHz, CDCl$_3$) δ −69.29 (S).

Embodiment 54 a24 (120.10 mg, 0.2 mmol), potassium acetate (19.6 mg, 0.2 mmol), absolute ethanol (2.0 mL, water ≤0.01 wt %), and methyl glycidyl ether b1 (52.9 mg, 0.6 mmol) are sequentially added to a 25 mL dry clean Schlenck tube with a magnetic stirrer to form a reaction system. The Schlenck tube is heated in a 90° C. oil bath for 35 hours, and TLC shows that the raw material is completely reacted to obtain a product system. The product system is stopped heating and cooled to a room temperature, and the solvent is removed under reduced pressure to give a residue, the residue is purified by silica gel column chromatography (hexane/EA=20/1) to obtain a pure product of 62.3 mg, with a yield of 75%.

Nuclear Magnetic Test Results of Product c22 (Ethyl 2-(1,3-dioxoisoindolin-2-yl)-3-phenyl-3-p-tolylpropanoate)

$^1$H NMR (500 MHz, CDCl$_3$) δ 7.83-7.69 (m, 2H), 7.69-7.62 (m, 2H), 7.50 (d, J=7.5 Hz, 1H), 7.41 (d, J=7.5 Hz, 1H), 7.33 (t, J=7.5 Hz, 1H), 7.27 (d, J=9.0 Hz, 1H), 7.22 (t, J=7.5 Hz, 0.5H), 7.17 (t, J=7.0 Hz, 1H), 7.11 (t, J=7.5 Hz, 1H), 6.99 (t, J=7.5 Hz, 0.5H), 6.93 (d, J=7.5 Hz, 1H), 5.78-5.71 (m, 1H), 5.33-5.23 (m, 1H), 4.13-3.98 (m, 2H), 2.32 (s, 1.5H), 2.13 (s, 1.5H), 1.06-0.98 (m, 3H). $^{13}$C NMR (125 MHz, CDCl$_3$) δ 168.43, 168.37, 167.49, 167.44, 142.03, 140.84, 138.75, 137.61, 136.46, 136.44, 134.11, 131.52, 131.45, 129.47, 129.32, 128.73, 128.57, 127.98, 127.83, 127.81, 127.70, 126.85, 123.50, 123.45, 77.41, 77.16, 76.91, 61.75, 61.71, 55.40, 55.26, 50.33, 50.29, 29.81, 21.14, 20.99, 13.83.

Embodiment 55 a25 (118.89 mg, 0.2 mmol), potassium acetate (19.6 mg, 0.2 mmol), absolute ethanol (2.0 mL, water ≤0.01 wt %), and methyl glycidyl ether b1 (52.9 mg, 0.6 mmol) are sequentially added to a 25 mL dry clean Schlenck tube with a magnetic stirrer to form a reaction system. The Schlenck tube is heated in a 90° C. oil bath for 35 hours, and TLC shows that the raw material is completely reacted to obtain a product system. The product system is stopped heating and cooled to a room temperature, and the solvent is removed under reduced pressure to give a residue, the residue is purified by silica gel column chromatography (hexane/EA=10/1) to obtain a pure product, with a yield of 91%.

Nuclear Magnetic Test Results of Product c23 (Ethyl 4-(2-(1,3-dioxoisoindolin-2-yl)-2-(ethoxycarbonyl) cyclopropyl) benzoate)

$^1$H NMR (500 MHz, CDCl$_3$) δ 8.02 (d, J=8.0 Hz, 2H), 7.92-7.91 (m, 2H), 7.79-7.77 (m, 2H), 7.68 (d, J=8.0 Hz, 2H), 4.38 (q, J=7.0 Hz, 1H), 3.84-3.76 (m, 2H), 3.17 (t, J=9.5 Hz, 1H), 2.51 (dd, J$_1$=6.5 Hz, J$_2$=9.0 Hz, 1H), 1.94 (dd, J$_1$=6.5 Hz, J$_2$=9.0 Hz, 1H), 1.40 (t, J=7.0 Hz, 3H), 0.78 (t, J=7.0 Hz, 3H). $^{13}$C NMR (125 MHz, CDCl$_3$) δ 168.22, 167.65, 166.66, 140.20, 134.56, 131.87, 129.91, 129.46, 123.76, 61.74, 61.07, 38.21, 33.48, 19.24, 14.50, 13.84.

Embodiment 56 a26 (107.64 mg, 0.2 mmol), potassium acetate (19.6 mg, 0.2 mmol), absolute ethanol (2.0 mL, water ≤0.01 wt %), and methyl glycidyl ether b1 (52.9 mg, 0.6 mmol) are sequentially added to a 25 mL dry clean Schlenck tube with a magnetic stirrer to form a reaction system. The Schlenck tube is heated in a 90° C. oil bath for 35 hours, and TLC shows that the raw material is completely reacted to obtain a product system. The product system is stopped heating and cooled to a room temperature, and the solvent is removed under reduced pressure to give a residue, the residue is purified by silica gel column chromatography (hexane/EA=20/1) to obtain a pure product, with a yield of 89%.

Nuclear Magnetic Test Results of Product c24
(Ethyl 1-benzoyl-4-p-tolylpiperidine-3-carboxylate)

$^1$H NMR (500 MHz, CDCl$_3$) δ 7.51-7.33 (m, 5H), 7.18-7.01 (m, 2H), 5.12-4.77 (m, 1H), 4.08-3.70 (m, 3H), 3.37-3.08 (m, 1H), 3.04-2.55 (m, 3H), 2.31 (s, 3H), 1.89-1.60 (m, 2H), 1.00-0.84 (m, 3H).

Embodiment 57 a27 (78.26 mg, 0.2 mmol), potassium acetate (19.6 mg, 0.2 mmol), absolute ethanol (2.0 mL, water ≤0.01 wt %), and methyl glycidyl ether b1 (52.9 mg, 0.6 mmol) are sequentially added to a 25 mL dry clean Schlenck tube with a magnetic stirrer to form a reaction system. The Schlenck tube is heated in a 90° C. oil bath for 35 hours, and TLC shows that the raw material is completely reacted to obtain a product system. The product system is stopped heating and cooled to a room temperature, and the solvent is removed under reduced pressure to give a residue, the residue is purified by silica gel column chromatography (hexane/EA=30/1) to obtain a pure product of 38.7 mg, with a yield of 95%.

Nuclear Magnetic Test Results of Product c25
(Ethyl 2-methyl-3-phenylbut-2-enoate)

$^1$H NMR (500 MHz, CDCl$_3$) δ 7.42-7.35 (m, 2H), 7.32-7.28 (m, 1H), 7.17 (d, J=7.0 Hz, 2H), 4.34-4.24 (m, 2H), 2.28 (d, J=1.5 Hz, 3H), 1.78 (d, J=1.5 Hz, 3H), 1.38 (t, J=7.0 Hz, 3H).

Embodiment 58 a28 (122.93 mg, 0.2 mmol), potassium acetate (19.6 mg, 0.2 mmol), absolute ethanol (2.0 mL, water ≤0.01 wt %), and methyl glycidyl ether b1 (52.9 mg, 0.6 mmol) are sequentially added to a 25 mL dry clean Schlenck tube with a magnetic stirrer to form a reaction system. The Schlenck tube is heated in a 90° C. oil bath for 35 hours, and TLC shows that the raw material is completely reacted to obtain a product system. The product system is stopped heating and cooled to a room temperature, and the solvent is removed under reduced pressure to give a residue, the residue is purified by silica gel column chromatography (hexane/EA=20/1) to obtain a pure product, with a yield of 85%.

Nuclear Magnetic Test Results of Product c26
(Ethyl 2-(1,3-dioxoisoindolin-2-yl)-5-(triisopropylsilyl)pent-4-ynoate)

$^1$H NMR (500 MHz, CDCl$_3$) δ 7.88-7.81 (m, 2H), 7.76-7.69 (m, 2H), 5.08 (dd, J=12.0, 5.0 Hz, 1H), 4.29-4.15 (m, 2H), 3.36 (dd, J=17.5, 12.0 Hz, 1H), 3.11 (dd, J=17.5, 5.0 Hz, 1H), 1.23 (t, J=7.0 Hz, 3H), 0.88-0.76 (m, 21H). $^{13}$C NMR (125 MHz, CDCl$_3$) δ 168.05, 167.31, 134.21, 132.02, 123.59, 102.79, 83.66, 62.28, 50.91, 20.86, 18.43, 18.42, 14.19, 11.11.

Embodiment 59 a29 (120.34 mg, 0.2 mmol), potassium acetate (19.6 mg, 0.2 mmol), absolute ethanol (2.0 mL, water ≤0.01 wt %), and methyl glycidyl ether b1 (52.9 mg, 0.6 mmol) are sequentially added to a 25 mL dry clean Schlenck tube with a magnetic stirrer to form a reaction system. The Schlenck tube is heated in a 90° C. oil bath for 35 hours, and TLC shows that the raw material is completely reacted to obtain a product system. The product system is stopped heating and cooled to a room temperature, and the solvent is removed under reduced pressure to give a residue, the residue is purified by silica gel column chromatography (hexane/EA=50/1) to obtain a pure product, with a yield of 93%.

Nuclear Magnetic Test Results of Product c27
(Ethyl 2-(4-isobutyl-2-((triisopropylsilyl) ethynyl) phenyl) propanoate)

$^1$H NMR (500 MHz, CDCl$_3$) δ 7.27-7.25 (m, 1H), 7.21 (d, J=8.0 Hz, 1H), 7.11-7.04 (m, 1H), 4.37 (q, J=7.0 Hz, 1H), 4.21-4.03 (m, 2H), 2.41 (d, J=7.0 Hz, 2H), 1.85 (dp, J=14.0, 7.0 Hz, 1H), 1.47 (d, J=7.0 Hz, 3H), 1.20 (t, J=7.0 Hz, 3H), 1.14 (s, 18H), 0.90 (d, J=7.0 Hz, 6H).

Embodiment 60

It differs from Embodiment 1 in that the epoxy compound used is b2, and the yield is 92%.

Embodiment 61

It differs from Embodiment 1 in that the epoxy compound used is b3, and the yield is 69%.

Embodiment 62

It differs from Embodiment 1 in that the epoxy compound used is b4, and the yield is 21%.

Embodiment 63

It differs from Embodiment 1 in that the epoxy compound used is b5, and the yield is 68%.

Embodiment 64

It differs from Embodiment 1 in that the epoxy compound used is b6, and the yield is 87%.

Embodiment 65

It differs from Embodiment 1 in that the epoxy compound used is b7, and the yield is 89%.

Embodiment 66

It differs from Embodiment 1 in that the epoxy compound used is b8, and the yield is 47%.

From the results of the above Embodiments, it can be seen that the method of the present application is applicable to a wide range of substrates and mild reaction conditions. The yield of some of the Embodiments is slightly lower, and the possible reason is that the reaction conditions need to be adjusted or the solvent and the like used needs to be adjusted.

From the above description, it can be seen that the Embodiments of the present application achieve the following technical effects:

The method provided in the present application is easy to operate; furthermore, for post-treatment, a pure product can be obtained only by means of a simple conventional separation step. Furthermore, due to the fact that the epoxy compound has a low cost, the production operation costs and the risk and cost of the treatment of three wastes can be greatly reduced. In addition, during use, the above-mentioned method has mild reaction conditions, is compatible with a variety of different substituents and functional groups, can achieve a good yield for amides of various structural types, and has a wide range of applicable substrates. That is, the present application provides an environmentally-friendly, economical and practical efficient method for alcoholysis of amide. The above-mentioned alcoholysis reaction of the present application is not affected by impurities in a C—H activation reaction system in the last step, thus saving an intermediate purification step, and the two steps of the reactions, i.e., C—H activation and amide alcoholysis, can be linked.

The above are only the preferred embodiments of the present application and not intended to limit the present application. For those skilled in the art, various modifications and changes can be made to the present application. Any modification, equivalent substitution and improvement made within the spirit and principle of the present application are intended to be included within the scope of protection of the present application.

What is claimed is:

1. A method for alcoholysis of an amide, the method comprising:
    mixing the amide-containing compound, the epoxy compound, a pH adjuster and a solvent to form an alkaline reaction system, the pH of the alkaline reaction system being 7.5-9.5;
    reacting the alkaline reaction system at 50° C.-150° C. to subject the amide-containing compound to alcoholysis, calculated in the molar ratio of the epoxy compound to an amide group, the ratio of the epoxy compound used to the amide-containing compound used is 1-5:1, the amide-containing compound has a formula I, the formula I is

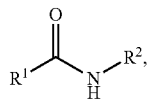

wherein the R¹, and the R² are each independently selected from any one of an alkyl group, an aryl group, a substituted alkyl group and a substituted aryl group; the epoxy compound has a formula II, the formula II is

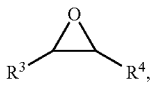

wherein the R³ and the R⁴ are each independently selected from any one of H, an alkyl group and an aryl group,
    the solvent is selected from any one or more of a group of methanol, ethanol, n-propanol, isopropanol, n-butanol, isobutanol, n-pentanol, isoamyl alcohol, ethylene glycol and glycerol.

2. The method according to claim 1, wherein the alkyl group is selected from any one of $C_1$-$C_{18}$ alkyl groups.

3. The method according to claim 1, wherein the alkyl group is selected from any one of $C_1$-$C_{18}$ alkyl groups.

4. The method according to claim 1, wherein the pH adjuster is a weak acid or a weak base.

5. The method according to claim 1, wherein the amide-containing compound is

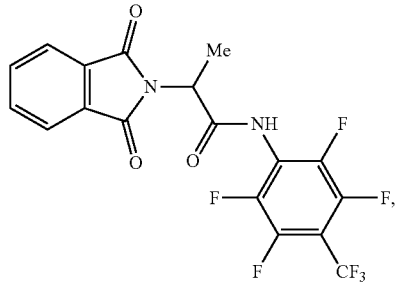 [SMILES: CC(C(=O)Nc1c(F)c(F)c(C(F)(F)F)c(F)c1F)N1C(=O)c2ccccc2C1=O]

the epoxy compound is methyl glycidyl ether, the pH adjuster is KOAc, and the solvent is ethanol.

6. The method according to claim 5, wherein the alkaline reaction system is reacted at 80° C.-100° C. to subject the amide-containing compound to alcoholysis.

7. The method according to claim 5, wherein after completion of the alcoholysis, the method further comprises:
    removing the solvent of the alcoholysis product under reduced pressure to obtain a residue;
    mixing the residue with water to form a mixture;
    adjusting the pH of the mixture to 3.5-4.5 and extracting with n-hexane to obtain an organic phase; and
    drying and filtering the organic phase.

8. The method according to claim 5, wherein after completion of the alcoholysis, the method further comprises:
    removing the solvent of the alcoholysis product under reduced pressure to obtain a residue;
    purifying the residue by silica gel column chromatography.

9. The method according to claim 2, wherein the substituted alkyl group has a main chain carbon number of any one of $C_1$-$C_{18}$.

10. The method according to claim 2, wherein the substituted alkyl group is a monosubstituted alkyl group or a polysubstituted alkyl group.

11. The method according to claim 2, wherein the substituent in the substituted alkyl group is selected from any one or a combination of more of a group of an aryl group, an aromatic heterocyclic substituent, a cycloalkane group, a heterocycloalkane group, an alkenyl group and an alkynyl group.

12. The method according to claim 4, the pH adjuster is seleced from any one or more of a group of $CF_3CO_2K$, $CF_3CO_2Na$, CsOAc, KOAc, NaOAc, LiOAc, $CsHCO_3$, $KHCO_3$, $NaHCO_3$, $LiHCO_3$, CsF, KF, NaF, LiF, $Cs_2CO_3$, $Na_2CO_3$, $Li_2CO_3$, $K_2HPO_4$, $Na_2HPO_4$, $Li_2HPO_4$, $K_3PO_4$, $Na_3PO_4$, sodium benzoate, tetramethylethylenediamine, N—N diisopropylethylamine and triethylamine.

* * * * *